(12) United States Patent
De Cupere et al.

(10) Patent No.: US 10,406,101 B2
(45) Date of Patent: Sep. 10, 2019

(54) PROCESS FOR THE PRODUCTION OF A SUBMICRON OIL IN WATER EMULSION

(71) Applicant: GlaxoSmithKline Biologicals S.A., Rixensart (BE)

(72) Inventors: Vinciane De Cupere, Rixensart (BE); Vincent Mancuso, Rixensart (BE)

(73) Assignee: GLAXOSMITHKLINE BIOLOGICALS S.A., Rixensart (BE)

( * ) Notice: Subject to any disclaimer, the term of this patent is extended or adjusted under 35 U.S.C. 154(b) by 147 days.

(21) Appl. No.: 14/679,198

(22) Filed: Apr. 6, 2015

(65) Prior Publication Data

US 2015/0209278 A1 Jul. 30, 2015

Related U.S. Application Data

(62) Division of application No. 13/702,691, filed as application No. PCT/EP2011/059489 on Jun. 8, 2011, now abandoned.

(30) Foreign Application Priority Data

Jun. 10, 2010 (GB) .................................. 1009676.6

(51) Int. Cl.
*A61K 9/107* (2006.01)
*A61K 47/06* (2006.01)
*A61K 47/22* (2006.01)
*A61K 39/39* (2006.01)
*A61K 9/00* (2006.01)
*A61K 39/00* (2006.01)

(52) U.S. Cl.
CPC .......... *A61K 9/1075* (2013.01); *A61K 9/0019* (2013.01); *A61K 9/107* (2013.01); *A61K 39/39* (2013.01); *A61K 47/06* (2013.01); *A61K 47/22* (2013.01); *A61K 2039/55588* (2013.01)

(58) Field of Classification Search
CPC ........ A61K 2039/55588; A61K 9/0019; A61K 9/107; A61K 9/1075; A61K 39/39; A61K 47/06; A61K 47/22
USPC .......................................... 424/278.1, 283.1
See application file for complete search history.

(56) References Cited

U.S. PATENT DOCUMENTS

| 4,816,247 | A | 3/1989 | Desai et al. |
| 6,168,718 | B1 | 1/2001 | Sutter et al. |
| 6,645,463 | B1 | 11/2003 | Counsell et al. |
| 10,213,383 | B2* | 2/2019 | Kraus .................... A61K 39/39 |
| 2005/0192222 | A1 | 9/2005 | Eibl |
| 2006/0263773 | A1 | 11/2006 | Tanaka |
| 2011/0162982 | A1* | 7/2011 | Kraus .................. A61K 9/0019 |
| | | | 206/223 |
| 2011/0165192 | A1* | 7/2011 | Rueckl ................ A61K 9/0019 |
| | | | 424/209.1 |
| 2012/0219587 | A1* | 8/2012 | D'Hondt ............ A61K 39/145 |
| | | | 424/210.1 |
| 2013/0129786 | A1* | 5/2013 | Kraus ................... A61K 39/39 |
| | | | 424/400 |

FOREIGN PATENT DOCUMENTS

| EP | 0 963 787 A1 | 12/1999 |
| JP | 2009-518302 | 5/2009 |
| JP | 2009-524595 | 7/2009 |
| JP | 2015200698 A | 11/2015 |
| KR | 20090083448 A | 8/2009 |
| WO | WO 1994/005298 | 3/1994 |
| WO | WO 2006/008504 | 1/2006 |
| WO | WO-2007064926 A2 * | 6/2007 ........... A61K 31/395 |
| WO | WO 2008/056263 A2 | 5/2008 |
| WO | WO 2011/067669 A2 | 6/2011 |

OTHER PUBLICATIONS

Rosalie J. Coté, Sterilization and Filtration (Unit 1.4), Current Protocols in Cell Biology (1999), 1.41.-1.4.21 [Retrieved from internet <URL: http://www.currentprotocols.com/WileyCDA/CPUnit/refId-cb0104.html >], 23 pages total.*
GE Healthcare Life Sciences, Capsule Filters, [Retrieved from internet <URL: http://www.gelifesciences.com/webapp/wcs/stores/servlet/catalog/en/GELifeSciences/products/AlternativeProductStructure_21521/ >], [Downloaded Jul. 20, 2017], 1 page.*
Lidgate, p. 860, col. 2, first and 2nd full paragraphs) (Lidgate et al., Sterile Filtration of a Parenteral Emulsion, Pharmaceutical Research (1992), 9 (7): 860-863.*
Pall Corporation, Sterile Large-Volume Filtration Samples [Retrieved from internet <URL: http://ru.pall.com/main/laboratory/sterile-large-volume-filtration-samples-52545.page >], [Downloaded Jul. 20, 2017], 3 pages.*
Barchfeld, G. L., et al., Enhancement of humoral response against human influenza vaccine with the simple submicron oil/water emulsion adjuvant MF59 *Vaccine* 1995 13(16):1557-1562.
Hung et al, The effect of oil components on the physicochemical properties and drug delivery of emulsions: Tocol emulsion versus lipid emulsion *International Journal of Pharmaceutics* 2007 335(1-2):193-202.

(Continued)

*Primary Examiner* — Bethany P Barham
*Assistant Examiner* — Miriam A Levin
(74) *Attorney, Agent, or Firm* — Birch, Stewart, Kolasch & Birch, LLP

(57) ABSTRACT

The present invention provides processes for the production of a submicron oil in water emulsion comprising the steps:
a. preparing a submicron oil in water emulsion;
b. pre-filtering the oil in water emulsion;
c. filtering the oil in water emulsion filtered according to step b) through a sterile grade filter;
d. filtering the oil in water emulsion filtered according to step c) through a filter separate to that of step b) or step c); and
e. filtering the oil in water emulsion filtered according to step d) through a sterile grade filter separate to that of steps b), c) and/or d).

15 Claims, No Drawings

(56) References Cited

OTHER PUBLICATIONS

Jornitz, et al, Considerations in sterile filtration, part II: The sterilizing filter and its organism challenge: A critique of regulatory standards *PDA Journal of Pharmaceutical Science and Technology* 2003 57(2):88-96.

Gary Ott, The adjuvant MF59: A 10-year Perspective *Methods in Molecular Medicine* 2000 42:211-228.

Guidance for Industry, Sterile Drug Products Produced by Aseptic Processing—Current Good Manufacturing Practice, U.S. Department of Health and Human Services Food and Drug Administration Center for Drug Evaluation and Research (CDER), Center for Biologics Evaluation and Research (CBER), Office of Regulatory Affairs (ORA), Sep. 2004.

Jornitz, Maik W., Filter Construction and Design, Adv Biochem Engin/Biotechnol (2006) 98: 105-123.

Filtration + Separation, 2008, p. 18-21.

* cited by examiner

PROCESS FOR THE PRODUCTION OF A SUBMICRON OIL IN WATER EMULSION

CROSS-REFERENCE TO RELATED APPLICATIONS

This application is a divisional application of U.S. patent application Ser. No. 13/702,691 which was filed 7 Dec. 2012, under 35 U.S.C. § 371 as a United States National Phase Application of International Patent Application Serial No. PCT/EP2011/059489 filed on Jun. 8, 2011, which claims the priority of GB 1009676.6 filed on Jun. 10, 2010.

TECHNICAL FIELD

The present invention relates to improved processes for the production of submicron oil in water emulsions, in particular, filtration of submicron oil in water emulsions.

BACKGROUND TO THE INVENTION

Methods of manufacture are disclosed in Ott et al., 2000 (The Adjuvant MF59: A 10-year Perspective. Vaccine Adjuvants: Preparation methods and Research Protocols [Methods in Molecular medicine, Vol. 42, Chapter 12, p211-228], Ott et al., 1995 (MF59—Design and Evaluation of a Safe and Potent Adjuvant for Human Vaccines: Vaccine Design, the Subunit and Adjuvant Approach [Pharmaceutical Biotechnology volume 6] eds. Powell & Newman, WO06/100110A1 and Lidgate et al., 1992 (Sterile Filtration of a Parenteral Emulsion. Pharmaceuticals Research 9(7): 860-863).

Oil in water emulsions can be used in vaccine/immunogenic compositions as adjuvants. As these emulsions are administered to humans it is necessary that the emulsions are sterile. Oil in water emulsions used as adjuvants are submicron emulsions and the oil droplets are sufficiently small to be sterile-filtered through 0.2 μm filtered. It is an object of the present invention to provide a process for the production of submicron oil in water emulsions and in particular filtration of oil in water emulsions.

SUMMARY OF THE INVENTION

The present invention relates to a process for production of submicron oil in water emulsion, in particular, filtration of submicron oil in water emulsions.

The present invention provides processes for the production of a submicron oil in water emulsion comprising the steps:
 a. preparing a submicron oil in water emulsion;
 b. pre-filtering the oil in water emulsion through sterile grade filter.
 c. filtering an oil in water emulsion filtered according to step b) through a sterile grade filter separate to that of step b).

DETAILED DESCRIPTION OF THE INVENTION

Oil in water emulsions, particularly submicron oil in water emulsions can be used as immunological adjuvants. Vaccine composition comprising said oil in water emulsions in combination with an antigen, such as an influenza antigens are administered parenterally and thus it is necessary for the oil in water emulsion to be sterile. The present inventors have demonstrated that in order to produce a sterile submicron oil in water emulsion is not sufficient to filter the emulsion through a single sterile grade filter. The inventors have shown that in order to provide a sterile oil in water emulsion it is necessary to prefilter the oil in water emulsion prior to filtration with a sterile grade filter.

Accordingly, the present invention provides a process for the production of a submicron oil in water emulsion comprising the steps:
 a. preparing a submicron oil in water emulsion;
 b. pre-filtering the oil in water emulsion through sterile grade filter.
 c. filtering an oil in water emulsion filtered according to step b) through a sterile grade filter separate to that of step b).

In a further embodiment of the invention there is provided a process for the production of a submicron oil in water emulsion comprising the steps:
 a. preparing a submicron oil in water emulsion;
 b. pre-filtering the oil in water emulsion through sterile grade filter;
 c. filtering an oil in water emulsion pre-filtered according to step b) through a filter separate to that of step b); and
 d. filtering an oil in water emulsion filtered according to step c) through a sterile grade filter separate to that of step b) or c).

In this particular embodiment, the filter used in step c) can have pores with the size ranging those of a sterile grade filter (i.e. about 0.2 μm), to a pore size of about 2 μm. In particular, the pore size of the filter used in step c) in the embodiment above ranges from the size of those of a sterile grade filter sterile grade filter to the size of about 1 μm. For example, the pore size of the filter used in step b) is about 2 μm, about 2.5 μm, about 1 μm, about 0.9 μm, about 0.8 μm, about 0.9 μm, about 0.7 μm, about 0.6 μm, about 0.5 μm, 0.45 μm or sterile grade for example about 0.2 μm, for example 0.22 μm.

A submicron oil in water emulsion is an oil in water emulsion in which the average droplet size is less than 1 μm. Methods of measuring droplet size are well known to the skilled person e.g. dynamic light scattering. Submicron oil in water emulsions can be produced by methods known to the person skilled on the art such as, but not limited to, high pressure homogenisation, for example using a microfluidiser. In a particular embodiment of the invention, submicron oil in water emulsions have an average oil droplet size of less than about 220 nm (0.2 μm), in particular between about 120 nm and about 180 nm.

By "sterile grade filter" it is meant a filter that produces a sterile effluent after being challenged by microorganisms at a challenge level of greater than or equal to $1\times10^7/cm^2$ of effective filtration area. Sterile grade filters are well known to the person skilled in the art of the invention and have a pore size of about 0.2 μm, and thus include filters with a pore size of about 0.22 μm.

The membranes of the filter can be made from any suitable material known to the skilled person, for example, but not limited to cellulose acetate, polyethersulfone (PES), polyvinylidene fluoride (PVDF), polytetrafluoroethylene (PTFE). In a particular embodiment of the invention one or more or all of the filter membranes of the present invention comprise polyethersulfone, for example hydrophilic polyethersulfone.

In a further embodiment of the invention there is provided a process as described herein comprising the steps;
 a. preparing a submicron oil in water emulsion;
 b. pre-filtering the oil in water emulsion;
 c. filtering an oil in water emulsion pre-filtered according to step b) through a sterile grade filter;

d. filtering an oil in water emulsion filtered according to step c) through a filter separate to that of step b) or step c);

e. filtering an oil in water emulsion filtered according to step d) through a sterile grade filter separate to that of step b), c) and/or d).

In this particular embodiment, the filter used in step b) and/or step d) can have pores with the size ranging from sterile grade filter (about 0.2 μm) to about 2 μm, in particular sterile grade filter to about 1 μm. For example, the pore size of the filter used in step b) and/or d) is about 2 μm, about 2.5 μm, about 1 μm, about 0.9 μm, about 0.8 μm, about 0.9 μm, about 0.7 μm, about 0.6 μm, about 0.5 μm, 0.45 μm or sterile grade for example about 0.2 μm, for example 0.22 μm. The filter used in steps b) and d) can have the same porosity to each other or have different pore sizes to each other.

In a particular embodiment of the invention, there is provided processes of the invention wherein the differential pressure of each filter is about 1 to about 1.5 bar, for example about 1 bar.

In a further embodiment, there is provided processes of the invention wherein filtration is performed at a temperature of between about 15° C. and about 30° C., about 16° C. and about 29° C., about 17° C. and about 28° C., about 16° C. and about 27° C., about 16° C. and about 28° C. or 22° C.±4° C.

In an embodiment of the invention, the submicron oil in water emulsions comprise between about 2% and about 15%, about 4% and about 12% oil, about 5% and about 10%, about 4% and about 6%, about 8% and about 12%, for example about 5% or 10% (v/v) oil.

In order for any oil in water composition to be suitable for human administration, the oil phase must comprise a metabolisable oil (i.e. biodegradable). The oil may be any vegetable oil, fish oil, animal oil or synthetic oil, which is not toxic to the recipient and is capable of being transformed by metabolism. Nuts, seeds, and grains are common sources of vegetable oils. Synthetic oils are also suitable. Accordingly, oil in water emulsions of the invention comprises a metabolisable oil, in a particular embodiment oil in water emulsions of the invention comprise squalene (for example between about 4% and 6% [v/v]).

Oil in water emulsions of the invention may also comprise a tocol. Tocols are well known in the art and are described in EP0382271. In particular, the tocol is α-tocopherol or a derivative thereof such as alpha-tocopherol succinate (also known as vitamin E succinate).

In a particular embodiment of the invention, there is provided an oil in water emulsion of the invention comprising squalene (for example about 5% [v/v]) and α-tocopherol (for example about 5% [v/v]).

Oil in water emulsions of the invention comprise one or more surfactants. Suitable surfactants are well known to the skilled person and include, but are not limited to polyoxyethylene (20) sorbitan monooleate (TWEEN 80, polysorbate 80), sorbitan trioleate (SPAN 85), phosphatidylcholine (lecithin), polyoxyethylene (12) cetostearyl ether and octoxynol-9 (TRITON X-100). In a particular embodiment of the invention oil in water emulsions comprise is polyoxyethylene (20) sorbitan monooleate (TWEEN 80, polysorbate 80). In a further embodiment, oil in water emulsions of the invention comprise polyoxyethylene (20) sorbitan monooleate (TWEEN 80) and a further surfactant, in particular sorbitan trioleate (SPAN 85).

In a particular embodiment of the invention the oil in water emulsion comprises a metabolisable oil (e.g. squalene), a tocol (e.g. α-tocopherol) and a surfactant (e.g. polyoxyethylene (20) sorbitan monooleate [TWEEN 80, polysorbate 80]).

In a further embodiment of the invention, oil in water emulsions of the invention comprise a metabolisable oil (e.g. squalene), a surfactant (e.g. polyoxyethylene (20) sorbitan monooleate [Polysorbate 80; TWEEN 80]), and optionally a second surfactant (e.g. sorbitan trioleate [SPAN 85]).

In a further embodiment of the invention, oil in water emulsions of the invention comprise a metabolisable oil (e.g. squalene), a polyoxyethylene alkyl ether hydrophilic non-ionic surfactant (e.g. polyoxyethylene (12) cetostearyl ether) and a hydrophobic non-ionic surfactant (e.g. polyoxyethylene (20) sorbitan monooleate [Polysorbate 80; TWEEN 80]), or sorbitan trioleate [SPAN 85]).

Embodiments herein relating to "vaccine compositions" of the invention are also applicable to embodiments relating to "immunogenic compositions" of the invention, and vice versa.

The terms "comprising", "comprise" and "comprises" herein are intended by the inventors to be optionally substitutable with the terms "consisting of", "consist of" and "consists of", respectively, in every instance.

The term "about" in relation to a numerical value x means x±5% or 10%.

Example

Method
Emulsification Process

Aqueous phase was prepared in tank 2, by mixing water for injection, phosphate buffer saline and Tween. Oil phase was prepared in tank 1, by mixing tocopherol and squalene. Both phases were stirred until homogeneity was obtained. The whole installation was flushed with nitrogen in order to avoid tocopherol oxidation.

High pressure homogenizer was fed with a membrane pump. Both phases were fed together, with the required flow rate ratio. Both phases first pass through a high shear homogenizer where a coarse emulsion was obtained. Then, in line with the high shear homogenizer, the product entered the high pressure homogenizer, were the fine emulsion was obtained.

At the outlet of the mixing device, the product was harvested in tank 3 (first pass). When tank 2 and 1 were empty, emulsion from tank 3 was directed towards the inlet of the mixing device and a second pass was performed. At the end of the second pass, the product is harvested in tank 2. When tank 3 was empty, the emulsion from tank 2 was directed towards the inlet of the mixing device and a third pass was performed. The emulsion was harvested in tank 3 and stored under nitrogen until filtration.

Filtration Process

Filtration is performed on two sterilizing filters comprising combined 0.5/0.2 μm membranes, at a maximum pressure of 1 bar, at a temperature ranging between 18 and 26° C., and for a contact time of maximum 3 hours. In order to demonstrate the efficiency of the filtration process, the filter membrane has to be challenged with *B. diminuta* suspended in the emulsion at a concentration of $10^7$ colony forming units (CFU)/cm$^2$ of membrane. Several set-up were tested in order to find the best configuration.

In the first set-up, the product was inoculated with *B. diminuta* bacteria at a concentration of $10^7$ CFU/cm$^2$ of membrane and filtrated on two 0.5/0.2 μm filters at a maximum pressure of 1 bar and at a temperature ranging between 18 and 26° C. The contact time between the inoculated product and the filter was 3 hours maximum.

Alternatively, the product was first prefiltrated on a 0.5 μm flat membrane. The product was then inoculated with *B. diminuta* bacteria at a concentration of $10^7$ CFU/cm$^2$ of membrane and filtrated on a 0.2 or on a 0.5/0.2 or on a 0.2/0.2 μm flat membrane(s) at a maximum pressure of 1 bar and at a temperature ranging between 18 and 26° C. The contact time between the inoculated product and the filter was 1.5 hours maximum.

Finally, the product was first prefiltrated on a capsule containing a 0.5 and a 0.2 μm filters. The product was then inoculated with *B. diminuta* bacteria at a concentration of $10^7$ CFU/cm$^2$ of membrane and filtrated on a 0.2 μm capsule at a maximum pressure of 1 bar and at a temperature ranging between 18 and 26° C. The contact time between the inoculated product and the filter was 3 hours maximum.

In all the cases, the filtrates were harvested after the last sterilizing membrane and the whole volumes were filtrated on 0.45 μm collection filters in order to identify the presence of *B. diminuta*. 0.45 μm filters were plated on a tryptic soy agar (TSA) plate and incubated for 7 days at 30° C. The plate where then visually inspected on day 2, 3, 4 and 7. If colonies were observed they were counted and identified.

Results

With no prefiltration or 0.5 μm prefiltration were applied, volume passed through the filter before clogging were smaller than the minimal retention volume needed to reach the target retention volume of 19.14 ml/cm$^2$ needed to meet the Bacterial Challenge Test (BCT), requirements of $10^7$ CFU/cm$^2$. When pre-filtration with a capsule containing 0.5/0.2 membranes was used as prefilter, then the retention volume increase up to 19.4 ml/cm$^2$ and no passage at all was observed.

| Cond. | Prefilter | Filter | Pressure | Set-up | Retention volume (ml/cm$^2$)[1] | Passage | BCT |
|---|---|---|---|---|---|---|---|
| 1 | none | (0.5/0.2 μm) × 2 | 1 bar | Flat membrane | 1.69 | 0 | Fail |
| 2 | none | (0.5/0.2 μm) × 2 | 1 bar | Flat membrane | 2.35 | 0 | Fail |
| 3 | 0.5 μm | 0.5/0.2 μm | 1 bar | Flat membrane | 3.67 | 0 | Fail |
| 4 | 0.5 μm | 0.2 μm | 1 bar | Flat membrane | 12.35 | 1 | Fail |
| 5 | 0.5 μm | 0.2/0.2 μm | 1 bar | Flat membrane | 0.07 | 0 | Fail |
| 6 | 0.5/0.2 μm | 0.5/0.2 μm | 1 bar | Capsule | >19.14 | 0 | Pass |
| 7 | 0.5/0.2 μm | 0.5/0.2 μm | 1 bar | Capsule | >19.14 | 0 | Pass |
| 8 | 0.5/0.2 μm | 0.5/0.2 μm | 1 bar | Capsule | >19.14 | 0 | Pass |

[1] in order to meet the BCT conditions ($10^7$ CFU/cm$^2$), the retention volume has to be higher than 19.14 ml/cm$^2$.

(1) in order to meet the BCT conditions ($10^7$ CFU/cm$^2$), the retention volume has to be higher than 19.14 ml/cm$^2$.

CONCLUSIONS

These results demonstrated that, for emulsions, performing a pre-filtration involving at least a 0.2 μm filter improved the capacity of the sterilizing filter and was a pre-requisite to demonstrate obtaining of a sterile effluent.

The invention claimed is:

1. A process for the production of a submicron biodegradable oil in water emulsion comprising the steps:
   a. preparing a submicron oil in water emulsion;
   b. pre-filtering the oil in water emulsion through a first filter having a pore size of about 0.5 μm;
   c. filtering the oil in water emulsion pre-filtered according to step b) through a second filter having a pore size of about 0.2 μm;
   d. filtering the oil in water emulsion filtered according to step c) through a third filter having a pore size of about 0.5 μm; and
   e. filtering the oil in water emulsion filtered according to step d) through a fourth filter having a pore size of about 0.2 μm
   wherein one or more filter membranes comprise hydrophilic polyethersulfone, and wherein the process is capable of passing a bacterial challenge test, the bacterial challenge test comprising the following additional steps:
   f. following step c) and prior to step d), the emulsion is inoculated with *B. diminuta* bacteria at a concentration of $10^7$ colony forming units/cm$^2$ of membrane, and
   g. filtration steps (d) and (e) are performed at a maximum pressure of 1 bar and a temperature ranging between 18 and 26 degrees Celsius,
   wherein steps (d) and (e) are capable of eliminating passage of the *B. diminuta* bacteria with a retention volume of at least 19.14 ml/cm$^2$ of membrane.

2. The process of claim 1 wherein the differential pressure of each filter is 1 to 1.5 bar.

3. The process of claim 1 where in filtration is performed between 15° C. and 30° C.

4. The process according to claim 1 wherein the oil in water emulsion comprises between 2% and 15% v/v oil.

5. The process according to claim 1 wherein the submicron biodegradable oil in water emulsion comprises squalene and one or more surfactants.

6. The process according to claim 5 wherein the submicron biodegradable oil in water emulsion comprises squalene, a-tocopherol and a surfactant.

7. The process according to claim 5 wherein at least one surfactant is polyoxyethylene (20) sorbitan monooleate.

8. The process of claim 5 wherein the submicron biodegradable oil in water emulsion comprises squalene, polyoxyethylene (20) sorbitan monooleate (TWEEN 80) and sorbitan trioleate (SPAN 85).

9. The process according to claim 5 wherein the submicron biodegradable oil in water emulsion comprises squalene, a polyoxyethylene alkyl ether hydrophilic non-ionic surfactant and a hydrophobic non-ionic surfactant.

10. The process according to claim 1, wherein steps b) and c) are performed using combined 0.5/0.2 μm membranes.

11. The process according to claim 1, wherein steps d) and e) are performed using combined 0.5/0.2 μm membranes.

12. The process according to claim 1, wherein the sterile grade filter of step c) and e) has a pore size of 0.2 μm.

13. The process according to claim 1, wherein the sterile grade filter of step c) and e) has a pore size of 0.22 μm.

14. The process according to claim 1, wherein the sterile grade filter of step b) and d) has a pore size of 0.5 μm.

15. The process according to claim 1, wherein the sterile grade filter of step b) and d) has a pore size of 0.45 μm.

* * * * *